United States Patent [19]

Klemm

[11] Patent Number: Plant 6,442

[45] Date of Patent: Dec. 6, 1988

[54] CARNATION NAMED KLETOUWI

[76] Inventor: Siegfried Klemm, Hanfacker 8, D 7000 Stuttgart 50, Fed. Rep. of Germany

[21] Appl. No.: 939,361

[22] Filed: Dec. 3, 1986

[51] Int. Cl.[4] ..... A01H 5/00
[52] U.S. Cl. ..... Plt./70
[58] Field of Search ..... Plt./70

*Primary Examiner*—Robert E. Bagwill
*Attorney, Agent, or Firm*—Charles W. Rummler

[57] ABSTRACT

A new variety of carnation plant distinguished by the very bright white coloring of its medium sized blooms which are borne on sturdy pedicels carried by very long, strong peduncles and by its continuous and profuse production of flowers.

BACKGROUND OF THE NEW PLANT

This new carnation cultivar originated at Stuttgart, West Germany, as a sport of an unpatented carnation variety names "Klemaxi", being grown in my greenhouses for the production of cut flowers, as well as for propagation and sale of plants to commercial growers. This sport was discovered by me in my greenhouses at Stuttgart in 1982 and was selected for propagation because of its bright, white coloration. Successive generations of this new cultivar propagated by means of cuttings have demonstrated that the new plant has not only retained the continuous and abundant production capability of its parent but also that its distinguishing characteristics hold true from generation to generation and appear to be firmly fixed.

1 Drawing Sheet

DESCRIPTION OF THE DRAWINGS

My new carnation variety is illustrated by the accompanying full color photographic drawing, which shows the inflorescence of a flower of a fully grown plant, the color rendition being as nearly true as it is reasonably possible to obtain by means of conventional photographic procedures.

DESCRIPTION OF THE NEW PLANT

The following is a detailed description of my new carnation cultivar based upon observation of plants grown under conventional greenhouse procedures, the color designation being according to The R.H.S. Colour Chart published by The Royal Horticultural Society of London, England.

THE PLANT

Origin: Sport.
Parentage: Klemaxi (unpatented).
Classification:
*Botanic.*—*Dianthus caryophyllus.*
*Commercial.*—Standard.
Form: Bush.
Height: About 150 cm. to about 170 cm.
Growth: Vigorous and upright with outstanding strength.
Branching: Normal.
Foliage:
*Quantity.*—Moderate.
*Leaf size.*—Moderate.
*Leaf shape.*—Oblong.
*Margine.*—Entire.
*Texture.*—Smooth.
*Color.*—Upper side — blue-green. Under side — blue-green.

THE BUD

Size: Medium, about 20 mm. in diameter and about 40 mm. long.
Form: Generally ovoid.

Opening rate: Moderate.
Color:
*When sepals first divide.*—White.
*When petals begin to unfurl.*—White.
Sepals:
*Condition.*—Curl back.
*Number.*—About 5-6.
*Color.*—Inside — light-green. Outside — gray-green.
Striae: Present.
Calyx:
*Shape.*—Campanulate.
*Size.*—Moderate, about 20 mm. broad and about 25 mm. long.
*Splitting.*—The calyx does not split.
*Aspect.*—Smooth.
*Peduncle.*—Rigid and erect.
*Length.*—About 80 cm.
*Color.*—Blue-green.

THE FLOWER

Blooming habit: Continuous and profuse.
Size of bloom: Medium.
*Diameter.*—About 75 mm. to about 80 mm.
*Depth.*—About 40 mm. to about 45 mm.
Borne: Singly on strong, upright stems.
Shape: Flat when the bloom opens. High center when the bloom matures.
Petalage:
*Number of petals.*—About 44 to about 50.
*Arrangement.*—Generally imbricated.
*Shape.*—Fan-shaped with serrated margins.
*Color.*—Outer petals — R.H.S. 155D. Inside petals — R.H.S. 155D. Reverse side — R.H.S. 155D.
*Texture.*—Soft.
*Appearance.*—Shiny.
Peduncle: Sturdy and upright.
*Length.*—About 80 cm.
*Color.*—Blue-green.
Persistence: The petals hang on and dry and the bloom stays upright.

Disease Resistance: Resistent to *Fusarium oxysporum* as observed in the Netherlands, France, Italy and Germany.

Fragrance: None.

Lasting quality:

*On plant.*—About 15 days.

*As a cut flower.*—About 12 days.

REPRODUCTIVE ORGANS

Stamens:

*Number.*—About 12 to about 15.

*Anthers.*—Color — yellow.

*Filaments.*—About 10 mm. to about 15 mm. Color — yellow.

*Pollen.*—Color — yellow.

Pistils: About 3 in number.

*Styles.*—Length — about 20 mm. to about 40 mm. Color — white.

*Stigmas.*—Color — white.

Fruit: Fertile.

*Shape.*—Ovoid.

*Color.*—Green/Brown at maturity.

I claim:

1. A new and distinct carnation cultivar, substantially as herein shown and described, characterized by its high productivity of bright white flowers borne singly on rigid, erect pedicels carried on a very long, sturdy and upright peduncle.

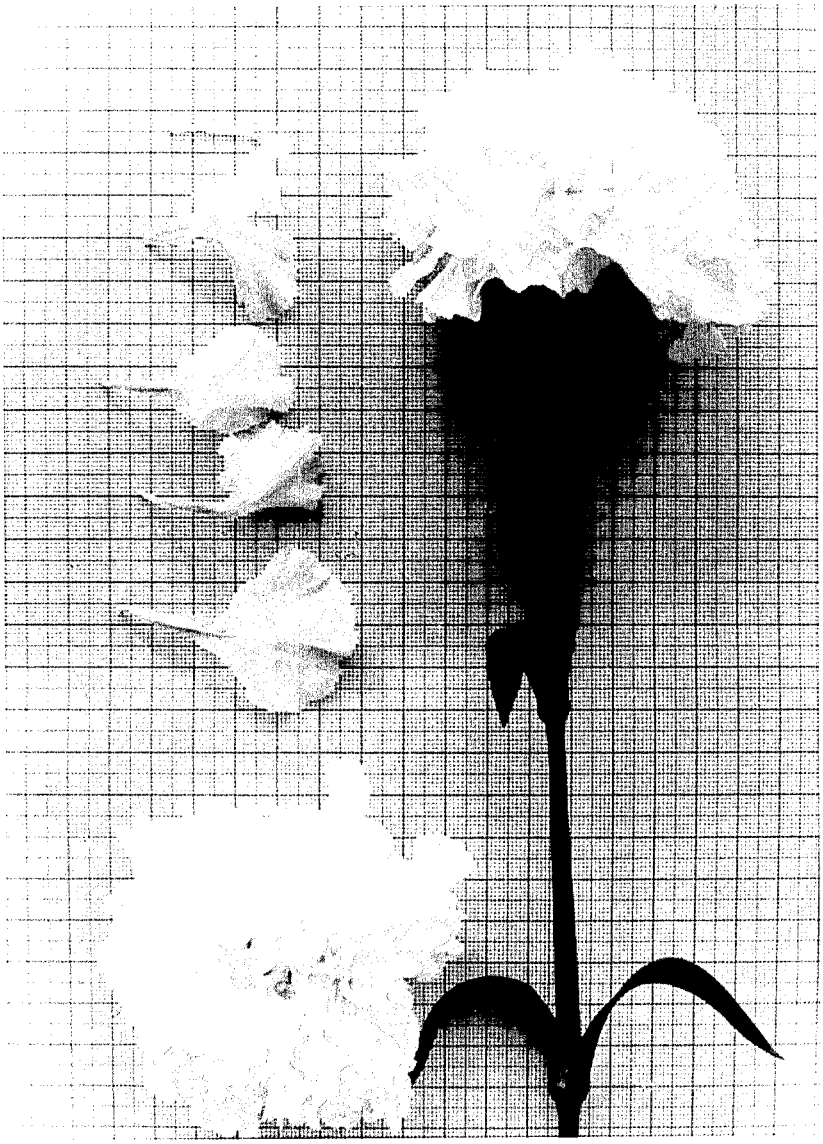

* * * * *